(12) United States Patent
Müller et al.

(10) Patent No.: US 6,726,902 B1
(45) Date of Patent: Apr. 27, 2004

(54) CLEANSING COSMETIC COMPOSITIONS AND USE

(75) Inventors: Rainer Müller, Leopoldshafen (DE); Myriam Mellul, L'Hay les Roses (FR)

(73) Assignee: L'Oreal (FR)

( * ) Notice: Subject to any disclaimer, the term of this patent is extended or adjusted under 35 U.S.C. 154(b) by 0 days.

(21) Appl. No.: 09/830,995

(22) PCT Filed: Oct. 26, 1999

(86) PCT No.: PCT/FR99/02601

§ 371 (c)(1),
(2), (4) Date: Oct. 3, 2001

(87) PCT Pub. No.: WO00/25735

PCT Pub. Date: May 11, 2000

(30) Foreign Application Priority Data

Nov. 4, 1998 (FR) ............................................. 98 13865

(51) Int. Cl.⁷ ................................................. A61K 7/08
(52) U.S. Cl. ................ 424/70.19; 424/70.1; 424/70.13; 424/70.21; 424/70.22; 424/70.24; 424/70.31
(58) Field of Search ................................ 424/401, 70.1, 424/70.13, 70.19, 70.21, 70.22, 70.24, 70.31

(56) References Cited

U.S. PATENT DOCUMENTS

| 2,528,378 A | 10/1950 | Mannheimer |
| 2,781,354 A | 2/1957 | Mannheimer |
| 4,540,567 A | * 9/1985 | Oneto et al. .................. 424/45 |
| 4,719,099 A | 1/1988 | Grollier et al. |
| 4,839,166 A | 6/1989 | Grollier et al. |
| 4,996,059 A | 2/1991 | Grollier et al. |
| 5,139,037 A | 8/1992 | Grollier et al. |
| 5,196,189 A | 3/1993 | Jacquet et al. |
| 5,776,444 A | * 7/1998 | Birtwistle et al. ........ 424/70.12 |
| 5,882,661 A | * 3/1999 | Dorogi et al. .............. 424/401 |

FOREIGN PATENT DOCUMENTS

| EP | 0 337 354 | 10/1989 |
| EP | 0 715 842 | 6/1996 |
| FR | 2 270 846 | 12/1975 |
| FR | 2 383 660 | 10/1978 |
| FR | 2 470 596 | 6/1981 |
| FR | 2 519 863 | 7/1983 |
| FR | 2 598 611 | 11/1987 |
| FR | 2 740 331 | 4/1997 |
| WO | WO 98/32420 | 7/1998 |

OTHER PUBLICATIONS

Harry's Cosmeticology, pp. 431–447 (1982).*

* cited by examiner

*Primary Examiner*—Jyothsna Venkat
(74) *Attorney, Agent, or Firm*—Finnegan, Henerson, Farabow, Garrett & Dunner, L.L.P.

(57) ABSTRACT

The invention concerns novel hair cleansing and conditioning compositions comprising, in a cosmetically suitable medium, (A) a washing base and (B) at least a $C_{12}-C_{26}$ carboxylic acid ester and a $C_{12}-C_{26}$ alcohol. The invention is useful for hair wash and hair care.

16 Claims, No Drawings

CLEANSING COSMETIC COMPOSITIONS AND USE

This application is a 371 of PCT/FR99/02601 filed on Oct. 26, 1999.

The present invention relates to novel cosmetic compositions with improved properties, intended both for cleaning and conditioning keratin materials such as the hair, and comprising, in a cosmetically acceptable aqueous vehicle, a washing base consisting of surfactants with detergent power, in which at least one ester of a $C_4$–$C_6$ carboxylic acid and of a $C_{12}$–$C_{26}$ alcohol is also present as conditioners. The invention also relates to the use of the said compositions in the abovementioned cosmetic application.

It is common to use detergent compositions (such as shampoos) based essentially on standard surfactants of anionic, nonionic and/or amphoteric type in particular, but more particularly of anionic type, to clean and/or wash keratin materials such as the hair. These compositions are applied to wet hair and the lather generated by massaging or rubbing with the hands removes, after rinsing with water, the various types of soiling which are initially present on the hair.

Admittedly these base compositions are of good washing power, but the intrinsic cosmetic properties associated with them nevertheless remain fairly poor, owing in particular to the fact that the relatively aggressive nature of such a cleaning treatment can, in the long run, lead to more or less pronounced damage to the hair fibre, this damage being associated in particular with the gradual removal of the lipids or proteins contained in or on the surface of this fibre.

Thus, in order to improve the cosmetic properties of the above detergent hair compositions, and more particularly those which are intended to be applied to sensitized hair (i.e. hair which has been damaged or made brittle, in particular under the chemical action of atmospheric agents and/or hair treatments such as permanent-waving, dyeing or bleaching), it is now common to introduce additional cosmetic agents known as conditioners into these compositions, these conditioners being intended mainly to repair or limit the harmful or undesirable effects induced by the various treatments or aggressions to which the hair fibres are subjected more or less repeatedly. These conditioners may, of course, also improve the cosmetic behaviour of natural hair.

With this aim, it is already being proposed to use silicones and more particularly insoluble silicones which become deposited on the keratin materials during rinsing. However, silicones have the drawback of being difficult to maintain in uniform dispersion in the medium.

It has already been proposed to use oils such as plant or animal oils or fatty acid esters as conditioners. However, conventional compositions have unsatisfactory detergent and foaming properties. Furthermore, keratin materials treated with these compositions usually have an unacceptable greasy feel.

The present invention is directed towards overcoming the drawbacks mentioned above by proposing conditioning and detergent compositions, which are sufficiently foaming, which have good conditioning properties, and in particular disentangling, softness and sheen properties, without imparting a greasy nature.

Thus, after considerable research-conducted in this matter, the Applicant has now found that by using a washing base and at least one liquid ester of a carboxylic acid containing from 4 to 6 carbon atoms and of an alcohol containing from 12 to 26 carbon atoms, it is possible to obtain stable detergent compositions which have excellent functional properties such as good intrinsic washing power and good foaming properties (foam abundance and strength and initiation of foaming). Furthermore, the compositions have good cosmetic properties, in particular the ease of styling, hold, liveliness and body of the treated hair.

The compositions in accordance with the invention give the hair, after rinsing, a noteworthy treating effect which is manifested in particular by an ease of disentangling, as well as by an increase in body, lightness, smoothness; softness and suppleness without any sensation of greasiness.

Thus, a subject of the present invention is novel detergent and conditioning cosmetic hair compositions, characterized in that they comprise, in a cosmetically acceptable aqueous medium, (A) a washing base and (B) at least one liquid ester of a carboxylic acid containing from 4 to 6 carbon atoms and of an alcohol containing from 12 to 26 carbon atoms.

A subject of the invention is also the cosmetic use of the above compositions for cleaning and/or conditioning the hair.

A—Washing Base:

The compositions in accordance with the invention necessarily comprise a washing base, which is generally aqueous.

The surfactant(s) forming the washing base can be chosen, indifferently, alone or as mixtures, from anionic, amphoteric, nonionic and cationic surfactants.

However, according to the invention, the washing base preferably comprises anionic surfactants or mixtures of anionic surfactants and amphoteric surfactants or nonionic surfactants.

Thus, according to the invention, the washing base can represent from 4% to 50% by weight, preferably from 6% to 35% by weight and even more preferably from 8% to 25% by weight, of the total weight of the final-composition.

The surfactants which are suitable for carrying out the present invention are in particular the following:

(i) Anionic Surfactant(s):

In the context of the present invention, their nature is not a truly critical feature.

Thus, as examples of anionic surfactants which can be used, alone or as mixtures, in the context of the present invention, mention may be made in particular (non-limiting list) of salts (in particular alkaline salts, especially sodium salts, ammonium salts, amine salts, amino alcohol salts or magnesium salts) of the following compounds: alkyl sulphates, alkyl ether sulphates, alkylamidoether sulphates, alkylarylpolyether sulphates, monoglyceride sulphates; alkyl sulphonates, alkyl phosphates, alkylamide sulphonates, alkylaryl sulphonates, α-olefin sulphonates, paraffin sulphonates; alkyl sulphosuccinates, alkyl ether sulphosuccinates, alkylamide sulphosuccinates; alkyl sulphosuccinamates; alkyl sulphoacetates; alkyl ether phosphates; acyl sarcosinates; acyl isethionates, acyl glutamates and N-acyltaurates, the alkyl or acyl radical of all of these various compounds preferably containing from 12 to 20 carbon atoms, and the aryl radical preferably denoting a phenyl or benzyl group. Among the anionic surfactants which can also be used, mention may also be made of fatty acid salts such as the salts of oleic, ricinoleic, palmitic and stearic acids, coconut oil acid or hydrogenated coconut oil acid; acyl lactylates in which the acyl radical contains 8 to 20 carbon atoms. Use may also be made of weakly anionic surfactants, such as alkyl-D-galactosiduronic acids and their salts, as well as polyoxyalkylenated alkyl ($C_6$–$C_{24}$)ether carboxylic acids, polyoxyalkylenated alkyl ($C_6$–$C_{24}$)aryl ether carboxylic acids, polyoxyalkylenated alkyl ($C_6$–$C_{24}$) amido ether carboxylic acids and their salts, in particular those containing from 2 to 50 ethylene oxide groups, and mixtures thereof.

Among the anionic surfactants, it is preferred to use according to the invention alkyl sulphate and alkyl ether sulphate salts and mixtures thereof.

(ii) Nonionic Surfactant(s):

Nonionic surfactants are likewise compounds that are well known per se (see in particular in this respect "Handbook of Surfactants" by M. R. Porter, published by Blackie & Son (Glasgow and London), 1991, pp. 116–178) and, in the context of the present invention, their nature is not a critical feature. Thus, they can be chosen in particular from (non-limiting list) polyethoxylated, polypropoxylated or polyglycerolated fatty acids, alkylphenols, α-diols or alcohols having a fatty chain containing, for example, 8 to 18 carbon atoms, it being possible for the number of ethylene oxide or propylene oxide groups to range in particular from 2 to 50 and for the number of glycerol groups to range in particular from 2 to 30. Mention may also be made of copolymers of ethylene oxide and of propylene oxide, condensates of ethylene oxide and of propylene oxide with fatty alcohols; polyethoxylated fatty amides preferably having from 2 to 30 mol of ethylene oxide, polyglycerolated fatty amides containing on average 1 to 5, and in particular 1.5 to 4, glycerol groups; polyethoxylated fatty amines preferably having 2 to 30 mol of ethylene oxide; oxyethylenated fatty acid esters of sorbitan having from 2 to 30 mol of ethylene oxide; fatty acid esters of sucrose, fatty acid esters of polyethylene glycol, alkylpolyglycosides, N-alkylglucamine derivatives, amine oxides such as $(C_{10}-C_{14})$alkylamine oxides or N-acylaminopropylmorpholine oxides. It will be noted that the alkylpolyglycosides constitute nonionic surfactants that are particularly suitable in the context of the present invention.

(iii) Amphoteric Surfactant(s):

The amphoteric surfactants, whose nature is not a critical feature in the context of the present invention, can be, in particular (non-limiting list), aliphatic secondary or tertiary amine derivatives in which the aliphatic radical is a linear or branched chain containing 8 to 22 carbon atoms and containing-at least one water-soluble anionic group (for example carboxylate, sulphonate, sulphate, phosphate or phosphonate); mention may also be made of $(C_8-C_{20})$alkylbetaines, sulphobetaines, $(C_8-C_{20})$alkylamido$(C_1-C_6)$alkylbetaines or $(C_8-C_{20})$alkylamido$(C_1-C_6)$alkylsulphobetaines.

Among the amine derivatives, mention may be made of the products sold under the name MIRANOL®, as described in U.S. Pat. Nos. 2,528,378 and 2,781,354 and with the structures:

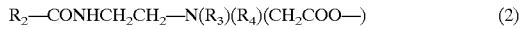

$$R_2-CONHCH_2CH_2-N(R_3)(R_4)(CH_2COO-) \quad (2)$$

in which: $R_2$ denotes an alkyl radical derived from an acid $R_2$—COOH present in hydrolysed coconut oil, a heptyl, nonyl or undecyl radical, $R_3$ denotes a β-hydroxyethyl group and $R_4$ a carboxymethyl group; and

$$R_{2'-CONHCH_2}CH_2-N(B)(C) \quad (3)$$

in which:

B represents —$CH_2CH_2OX'$, C represents—$(CH_2)_z$—Y', with z=1 or 2,

X' denotes the —$CH_2CH_2$—COOH group or a hydrogen atom,

Y' denotes —COOH or the —$CH_2$—CHOH—$SO_3H$ radical, $R_{2'}$ denotes an alkyl radical of an acid $R_9$ —COOH present in coconut oil or in hydrolysed linseed oil, an alkyl radical, in particular a $C_7$, $C_9$, $C_{11}$ or $C_{13}$ alkyl radical, a $C_{17}$ alky radical and its iso form, or an unsaturated $C_{17}$ radical.

These compounds are classified in the CTFA dictionary, 5th edition, 1993, under the names Disodium Cocoamphodiacetate, Disodium Lauroamphodiacetate, Disodium Caprylamphodiacetate, Disodium Capryloamphodiacetate, Disodium Cocoamphodipropionate, Disodium Lauroamphodipropionate, Disodium Caprylamphodipropionate, Disodium Capryloamphodipropionate, Lauroamphodipropionic acid, and Cocoamphodipropionic acid. By way of example, mention may be made of the cocoamphodiacetate sold under the trade name MIRANOL® C2M concentrate by the company Rhodia Chimie.

In the compositions in accordance with the invention, mixtures of surfactants and in particular mixtures of anionic surfactants and of amphoteric or nonionic surfactants are preferably used. One mixture which is particularly preferred is a mixture consisting of at least one anionic surfactant and at least one amphoteric surfactant.

An anionic surfactant chosen from sodium, triethanolamine or ammonium $(C_{12}-C_{14})$ alkyl sulphates, sodium $(C_{12}-C_{14})$ alkyl ether sulphates oxyethylenated with 2.2 mol of ethylene oxide, sodium cocoyl isethionate and sodium alpha-$(C_{14}-C_{16})$ olefin sulphonate and mixtures thereof with:

either an amphoteric surfactant such as the amine derivatives known as disodium cocoamphodipropionate or sodium cocoamphopropionate sold in particular by the company Rhodia Chimie under the trade name "MIRANOL® C2M CONC." as an aqueous solution containing 38% active material or under the name MIRANOL® C32;

or an amphoteric surfactant of zwitterionic type such as alkylbetaines, in particular the cocoylbetaine sold under the name "DEHYTON® AB 30" as an aqueous solution containing 32% AM by the company Henkel or alkylamidoalkylbetaines such as TEGOBETAINE® F50 sold by the company Goldschmidt; is preferably used.

(iv) Cationic Surfactants:

Among the cationic surfactants, mention may be made in particular of (non-limiting list): optionally polyoxyalkylenated primary, secondary or tertiary fatty amine salts; quaternary ammonium salts such as tetraalkylammonium, alkylamidoalkyltrialkyl-ammonium, trialkylbenzyl-ammonium, trialkylhydroxyalkyl-ammonium or alkylpyridinium chlorides or bromides; imidazoline derivatives; or amine oxides of cationic nature.

It will be noted that the cationic surfactants, the use of which is not excluded, do not constitute preferred surfactants for carrying out the present invention.

B—Liquid Esters

The compositions according to the invention necessarily comprise at least one liquid ester of a carboxylic acid containing from 4 to 6 carbon atoms and of an alcohol containing from 12 to 26 carbon atoms. These esters are insoluble in water at a concentration of greater than 0.1% at 25° C. They are liquid at ambient temperature below 30° C.

The liquid esters according to the invention preferably have the following formula:

$$R_1COOR_2 \quad (I)$$

in which:

R$_1$ denotes a linear or branched, optionally mono- or polyhydroxylated hydrocarbon-based radical containing from 3 to 5 carbon atoms, R$_2$ denotes a linear or branched, optionally mono- or polyhydroxylated hydrocarbon-based radical containing from 12 to 26 carbon atoms and preferably containing from 16 to 22 carbon atoms, R$_1$ preferably denotes a branched alkyl radical containing from 3 to 5 carbon atoms, and more particularly a tert-butyl radical, R$_2$ preferably denotes a saturated or unsaturated alkyl radical containing from 12 to 26 carbon atoms, which is more particularly branched and even more particularly chosen from tridecyl, isocetyl, isostearyl, octyldodecyl and isoarachidyl radicals.

The liquid esters that are particularly preferred are isostearyl neopentanoate (formula (I) in which R$_1$=tert-butyl and R$_2$=isostearyl), tridecyl neopentanoate, isocetyl neopentanoate and isoarachidyl neopentanoate.

The liquid ester(s) defined above may be used in the compositions in accordance with the invention in concentrations generally of between 0.1% and 20% and preferably between 0.2% and 10% by weight relative to the total weight of the composition and even more particularly from 0.5% to 5% by weight.

The cosmetically acceptable aqueous medium may consist solely of water or of a mixture of water and a cosmetically acceptable solvent such as a C$_1$–C$_4$ lower alcohol, for instance ethanol, isopropanol, tert-butanol or n-butanol; alkylene glycols, for instance propylene glycol, or glycol ethers.

The detergent compositions according to the invention have a final pH generally of between 3 and 10. This pH is preferably between 5 and 8. The pH may conventionally be adjusted to the desired value by adding a base (organic or inorganic) to the composition, for example aqueous ammonia or a primary, secondary or tertiary (poly)amine such as monoethanolamine, diethanolamine, triethanolamine, isopropanolamine or 1,3-propanediamine, or alternatively by adding an inorganic or organic acid, preferably a carboxylic acid such as, for example, citric acid.

In addition to the combination defined above, the compositions in accordance with the invention may contain viscosity regulators such as electrolytes or thickeners. Mention may be made in particular of sodium chloride, sodium xylenesulphonate, scleroglucans, xanthan gums, fatty acid alkanolamides, alkyl ether carboxylic acid alkanolamides optionally oxyethylenated with up to 5 mol of ethylene oxide, such as the product sold under the name "AMINOLA 15" by the company Chem Y. crosslinked polyacrylic acids and crosslinked acrylic acid/C$_{10}$–C$_{30}$ alkyl acrylate copolymers. These viscosity regulators are used in the compositions according to the invention in proportions which may be up to 10% by weight relative to the total weight of the composition.

The compositions in accordance with the invention may also contain up to 5% of nacreous agents or opacifiers that are well known in the state of the art, such as, for example, C$_{16}$ higher fatty alcohols, sodium or magnesium palmitate, sodium or magnesium stearate or hydroxystearate, fatty-chain acyl derivatives such as the monostearates or distearates of ethylene glycol or of polyethylene glycol, and fatty-chain ethers such as, for example, distearyl ether or 1-(hexadecyloxy)-2-octadecanol.

The compositions in accordance with the invention may also optionally contain other agents whose effect is to improve the cosmetic properties of the hair or the skin without, however, adversely affecting the stability of the compositions. Mention may be made in this respect of cationic surfactants, anionic, nonionic, cationic or amphoteric polymers, proteins, protein hydrolysates, ceramides, pseudoceramides, fatty acids containing linear or branched C$_{16}$–C$_{40}$ chains, such as 18-methyleicosanoic acid, hydroxy acids, vitamins, panthenol, volatile or non-volatile silicones, which may be soluble or insoluble in the medium, plant oils and synthetic oils, and mixtures thereof.

The conditioners of cationic polymer type which may be used in accordance with the present invention may be chosen from any of those already known per se as improving the cosmetic properties of hair treated with detergent compositions, i.e., in particular, those disclosed in patent application EP-A-0 337 354 and in French patent applications FR-A-2 270 846, FR-A-2 383 660, FR-A-2 598 611, FR-A-2 470 596 and FR-A-2 519 863.

Even more generally, for the purposes of the present invention, the expression "cationic polymer" denotes any polymer containing cationic groups and/or groups which may be ionized into cationic groups.

Among all the cationic polymers which may be used in the context of the present invention, it is preferred to use quaternary cellulose ether derivatives such as the products sold under the name "JR 400" by the company Union Carbide Corporation, cyclopolymers, in particular diallyldimethylammonium salt homopolymers, and copolymers of diallyldimethylammonium salt and of acrylamide, in particular the chlorides, sold under the names "MERQUAT 100", "MERQUAT 550"and "MERQUAT S" by the company Merck, and cationic polysaccharides and more particularly guar gums modified with 2,3-epoxypropyltrimethylammonium chloride, sold, for example, under the name "JAGUAR C13S" by the company Meyhall.

According to the invention, the cationic polymer(s) may represent from 0.001% to 10% by weight, preferably from 0.005% to 5% by weight and even more preferably from 0.01% to 3% by weight relative to the total weight of the final composition.

The compositions according to the invention may also contain foam synergists such as C$_{10}$–C$_{18}$ 1,2-alkanediols or fatty alkanolamides derived from mono- or diethanolamine.

Needless to say, a person skilled in the art will take care to select this or these optional complementary compounds and/or the amounts thereof such that the advantageous properties intrinsically associated with the combination (washing base+esters according to the invention) in accordance with the invention are not, or are not substantially, adversely affected by the addition or additions envisaged.

These compositions can be in the form of more or less thickened liquids, creams or gels and are mainly suitable for washing and caring for the hair.

When the compositions in accordance with the invention are used as standard shampoos, they are simply applied to wet hair and the lather generated by massaging or friction with the hands is then removed, after optionally leaving it to stand on the hair for a period of time, by rinsing with water, it being possible for the operation to be repeated one or more times.

A subject of the invention is also a process for washing and conditioning, which consists in applying an effective amount of a composition as defined above to the said wet materials, and then in rinsing them with water after optionally leaving the composition to stand on the materials for a period of time.

A concrete, but in no way limiting, example illustrating the invention will now be given.

EXAMPLE 1

Two shampoo compositions, one in accordance with the invention (composition A) and the other a comparative composition (composition B), were prepared:

| | A<br>Invention | B<br>Comparative |
|---|---|---|
| Sodium lauryl ether sulphate (70/30 C12/C14) containing 2.2 mol of ethylene oxide (as an aqueous solution containing 70% AM) (AM = active material) | 12.6 gAM | 12.6 gAM |
| Disodium cocoamphodiacetate (Miranol C2M conc. NP (*) (as an aqueous solution containing 38% AM) | 2.7 gAM | 2.7 gAM |
| Isostearyl neopentanoate | 1 g | — |
| Cationic cellulose gum (Polymer JR 400 from Union Carbide) | 0.2 g | 0.2 g |
| Ethylene glycol distearate | 1.5 g | 1.5 g |
| NaCl | 1.1 g | 1.1 g |
| Sodium cetearyl sulphate (90% AM) | 0.7 gAM | 0.7 gAM |
| Coconut acid monoisopropanolamide | 1.5 g | 1.5 g |
| Fragrance, preserving agent | qs | qs |
| Citric acid | 0.6 g | 0.6 g |
| Demineralized water qs | 100 g | 100 g |

(*) Miranol C2M conc. sold by Rhodia Chimie

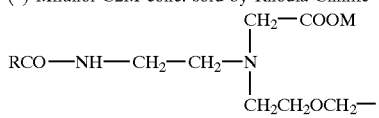

R denotes a mixture of coconut-based $C_8$–$C_{18}$ alkyl radicals
M represents Na Shampooing was carried out by applying about 12 g of composition A to premoistened sensitized hair. The shampoo is worked into a lather and is then rinsed out thoroughly with water.

The same procedure as above is carried out with the comparative composition B.

A panel of experts evaluated the foaming properties and the cosmetic properties of the two compositions.

The experts indicate that the initiation of foaming is very easy and the foam is more airy with composition A according to the invention.

Wet hair treated with composition A disentangles more easily and is more supple. Dried hair is smoother and has more body and manageability.

EXAMPLE 2

A shampoo composition in accordance with the invention was prepared:

| | |
|---|---|
| Sodium lauryl ether sulphate (70/30 C12/C14) containing 2.2 mol of ethylene oxide (as an aqueous solution containing 70% AM) (AM = active material) | 12.6 gAM |
| Disodium cocoamphodiacetate (Miranol C2M conc. NP (*) (as an aqueous solution containing 38% AM) | 2.7 gAM |
| Tridecyl neopentanoate | 1.5 g |
| Cationic cellulose gum (Polymer JR 400 from Union Carbide) | 0.2 g |
| Ethylene glycol distearate | 1.5 g |
| Sodium cetearyl sulphate (90% AM) | 0.7 gAM |
| Coconut acid monoisopropanolamide | 4 g |
| Fragrance, preserving agent | qs |

-continued

| | |
|---|---|
| NaOH | 0.1 g |
| Citric acid | 0.55 g |
| Demineralized water qs | 100 g |

(*) Miranol C2M conc. sold by Rhodia Chimie

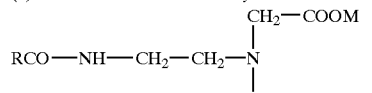

R denotes a mixture of coconut-based $C_8$–$C_{18}$ alkyl radicals
M represents Na A shampoo wash was carried out by applying about 12 g of composition A to sensitized hair which was made wet beforehand. The shampoo is worked into a lather and is then rinsed out thoroughly with water.

The initiation of foaming is very easy and the foam is airy.

Wet hair treated with the composition disentangles easily and is supple. Dried hair is smooth and has body and manageability.

What is claimed is:

1. A process for washing and conditioning a keratin material, said process comprising:
   (A) applying to said keratin material an effective amount of a composition comprising, in a cosmetically acceptable aqueous medium:
      (1) a washing base and
      (2) at least one liquid ester obtained by reacting at least one ($C_4$–$C_6$) carboxylic acid with at least one ($C_{12}$–$C_{26}$) alcohol,
   (B) optionally leaving said composition to act for a period of time, and
   (C) rinsing said keratin material with water.

2. A process for washing and conditioning a keratin material, said process comprising:
   (A) applying to said keratin material an effective amount of a composition comprising, in a cosmetically acceptable aqueous medium:
      (1) a washing base and
      (2) at least one liquid ester chosen from esters of formula (I):

$$R_1COOR_2 \qquad (I)$$

wherein:
      $R_1$ is chosen from a branched ($C_3$–$C_5$) hydrocarbon-based group, a monohydroxylated branched ($C_3$–$C_5$) hydrocarbon-based group, and a polyhydroxylated branched ($C_3$–$C_5$) hydrocarbon-based group, and
      $R_2$ is chosen from a linear ($C_{12}$–$C_{26}$) hydrocarbon-based group, a branched ($C_{12}$–$C_{26}$) hydrocarbon-based group, a monohydroxylated ($C_{12}$–$C_{26}$) hydrocarbon-based group, a monohydroxylated branched ($C_{12}$–$C_{26}$) hydrocarbon-based group, a polyhydroxylated linear ($C_{12}$–$C_{26}$) hydrocarbon-based group, and a polyhydroxylated branched ($C_{12}$–$C_{26}$) hydrocarbon-based group.
   (B) optionally leaving said composition to act for a period of time, and
   (C) rinsing said keratin material with water.

3. A process according to claim 2, wherein said keratin material is hair.

4. A process according to claim 3, wherein said $R_1$ is chosen from a branched ($C_3$–$C_5$) alkyl group, a monohydroxylated branched ($C_3$–$C_5$) alkyl group, and a polyhydroxylated branched ($C_3$–$C_5$) alkyl group and said $R_2$ is chosen from a linear ($C_{12}$–$C_{26}$) alkyl group, a branched ($C_{12}$–$C_{26}$) alkyl group, a monohydroxylated linear ($C_{12}$–$C_{26}$) alkyl group, a monohydroxylated branched ($C_{12}$–$C_{26}$) alkyl group, a polyhydroxylated linear ($C_{12}$–$C_{26}$) alkyl group, and a polyhydroxylated branched ($C_{12}$–$C_{26}$) alkyl group.

5. A process according to claim 4, wherein said R2 is chosen from a branched ($C_{12}$–$C_{26}$) alkyl group, a monohydroxylated branched ($C_{12}$–$C_{26}$) alkyl group, and a polyhydroxylated branched ($C_{12}$–$C_{26}$) alkyl group.

6. A process according to claim 3, wherein said $R_2$ is a tertbutyl group.

7. A process according to claim 3, wherein said $R_2$ is chosen from a tridecyl group, an isocetyl group, an isostearyl group, an octyldodecyl group, and an isoarachidyl group.

8. A process for washing a keratin material, said process comprising:
(A) applying to said keratin material an effective amount of a composition comprising, in a cosmetically acceptable aqueous medium:
(1) a washing base and
(2) at least one liquid ester chosen from esters of formula (I):

$$R_1COOR_2 \qquad (I)$$

wherein:
$R_1$ is chosen from a hydrocarbon based group, a branched ($C_3$–$C_5$) hydrocarbon-based group, a monohydroxylated branched ($C_3$–$C_5$) hydrocarbon-based group, and a polyhydroxylated branched ($C_3$–$C_5$) hydrocarbon-based group, and
$R_2$ is chosen from a linear ($C_{12}$–$C_{26}$) hydrocarbon-based group, a branched ($C_{12}$–$C_{26}$) hydrocarbon-based group, a monohydroxylated linear ($C_{12}$–$C_{26}$) hydrocarbon-based group, a monohydroxylated branched ($C_{12}$–$C_{26}$) hydrocarbon-based group, a polyhydroxylated linear ($C_{12}$–$C_{26}$) hydrocarbon-based group, and a polyhydroxylated branched ($C_{12}$–$C_{26}$) hydrocarbon-based group.

(B) optionally leaving said composition to wash for a period of time, and
(C) rinsing said keratin material with water.

9. A process according to claim 8, wherein said keratin material is hair.

10. A process for conditioning a keratin material, said process comprising:
(A) applying to said keratin material an effective amount of a composition comprising, in a cosmetically acceptable aqueous medium:
(1) a washing base and
(2) at least one liquid ester chosen from esters of formula (I):

$$R_1COOR_2 \qquad (I)$$

wherein:
$R_1$ is chosen from a branched (C3–C5) hydrocarbon-based group, a monohydroxylated branched ($C_3$–$C_5$) hydrocarbon-based group, and a polyhydroxylated branched ($C_3$–$C_5$) hydrocarbon-based group, and
$R_2$ is chosen from a linear ($C_{12}$–$C_{26}$) hydrocarbon-based group, a branched ($C_{12}$–$C_{26}$) hydrocarbon-based group, a monohydroxylated linear ($C_{12}$–$C_{26}$) hydrocarbon-based group, a monohydroxylated branched ($C_{12}$–$C_{26}$) hydrocarbon-based group, a polyhydroxylated linear ($C_{12}$–$C_{26}$) hydrocarbon-based group, and a polyhydroxylated branched ($C_{12}$–$C_{26}$) hydrocarbon-based group.

(B) optionally leaving said composition to condition for a period of time, and
(C) rinsing said keratin material with water.

11. A process according to claim 10, wherein said keratin material is hair.

12. A process for washing a keratin material, said process comprising:
(A) applying to said keratin material an effective amount of a composition comprising, in a cosmetically acceptable aqueous medium:
(1) a washing base and
(2) at least one liquid ester obtained by reacting at least one ($C_4$–$C_6$) carboxylic acid with at least one ($C_{12}$–$C_{26}$) alcohol,
(B) optionally leaving said composition to wash for a period of time, and
(C) rinsing said keratin material with water.

13. A process according to claim 12, wherein said keratin material is hair.

14. A process for conditioning a keratin material, said process comprising:
(A) applying to said keratin material an effective amount of a composition comprising, in a cosmetically acceptable aqueous medium:
(1) a washing base and
(2) at least one liquid ester obtained by reacting at least one ($C_4$–$C_6$) carboxylic acid with at least one ($C_{12}$–$C_{26}$) alcohol,
(B) optionally leaving said composition to condition for a period of time, and
(C) rinsing said keratin material with water.

15. A process according to claim 14, wherein said keratin material is hair.

16. A process according to claim 1, wherein said keratin material is hair.

* * * * *

UNITED STATES PATENT AND TRADEMARK OFFICE
CERTIFICATE OF CORRECTION

PATENT NO.      : 6,726,902 B1
DATED           : April 27, 2004
INVENTOR(S)     : Rainer Müller and Myriam Mellul It is certified that error appears in the above-identified patent and that said Letters Patent is hereby corrected as shown below:

Title page,
Item [73], Assignee, "L'Oreal (FR)" should read -- L'Oreal S.A. (FR) --
Item [57], ABSTRACT,
Line 3, "$C_{12}$-$C_{26}$" should read -- $C_4$-$C_6$ --.
Line 4, "$C_{12}$-$C_{26}$" should read -- $C_{12}$-$C_{26}$ --.

Column 8,
Line 55, "monohydroxylated ($C_{12}$-$C_{26}$)" should read -- monohydroxylated linear ($C_{12}$-$C_{26}$) --.
Line 60, "group." should read -- group, --.

Column 9,
Line 9, "R2" should read -- $R_2$ --.
Line 13, "$R_2$" should read -- $R_1$ --.
Line 29, after "from" delete "a hydrocarbon based group, --.
Line 41, "group." should read -- group, --.

Column 10,
Line 1, "(C3-C5)" should read -- ($C_3$-$C_5$) --.
Line 15, "group." should read -- group, --.

Signed and Sealed this

Sixth Day of July, 2004

JON W. DUDAS
*Acting Director of the United States Patent and Trademark Office*